(12) United States Patent
Sogaro

(10) Patent No.: US 8,499,976 B2
(45) Date of Patent: Aug. 6, 2013

(54) MULTICHAMBER DISPENSING DEVICE

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 1917 days.

(21) Appl. No.: 11/485,887

(22) Filed: Jul. 13, 2006

(65) Prior Publication Data
US 2007/0017931 A1    Jan. 25, 2007

(30) Foreign Application Priority Data

Jul. 22, 2005 (EP) ..................................... 05015995

(51) Int. Cl.
*B67D 7/70* (2010.01)
(52) U.S. Cl.
USPC ..................................... 222/137; 222/153.07
(58) Field of Classification Search
USPC ................. 222/137, 153.07; 215/256; 433/90
See application file for complete search history.

(56) References Cited

U.S. PATENT DOCUMENTS

| | | | |
|---|---|---|---|
| 3,073,472 A | 1/1963 | Williams | |
| 4,538,920 A * | 9/1985 | Drake | 222/137 |
| 4,753,536 A * | 6/1988 | Spehar et al. | 222/137 |
| 5,033,650 A * | 7/1991 | Colin et al. | 222/137 |
| 5,335,827 A | 8/1994 | Gentile | |
| 5,401,169 A | 3/1995 | Fleisher et al. | |
| 5,443,183 A | 8/1995 | Jacobsen et al. | |
| 6,547,101 B1 | 4/2003 | Sogaro | |
| 6,613,021 B2 | 9/2003 | Sogaro | |
| 6,698,622 B2 * | 3/2004 | Sawhney et al. | 222/137 |
| 2003/0121936 A1 * | 7/2003 | De Laforcade | 222/153.07 |

FOREIGN PATENT DOCUMENTS

EP    1 203 593 A1    5/2002

* cited by examiner

*Primary Examiner* — Kevin P Shaver
*Assistant Examiner* — Daniel R Shearer
(74) *Attorney, Agent, or Firm* — Quarles & Brady LLP

(57) ABSTRACT

A multichamber dispensing device for dispensing a mixture consisting of a plurality of substances includes a receptacle unit (10) with several chambers that are aligned parallel in relation to each other. Each chamber has an open first end for inserting a piston and a second end having an outlet opening. A dispensing unit (30) including a dispensing channel and an adapter section (36) is connected to the receptacle unit (10). The adapter section includes at least one detachable separating element (38) which protrudes radially to the inside and interacts with at least one locking means of the receptacle unit (10), so that after loosening the separating element (38), the dispensing unit (30) opposite the receptacle unit (10) can be shifted in an axial direction.

14 Claims, 3 Drawing Sheets

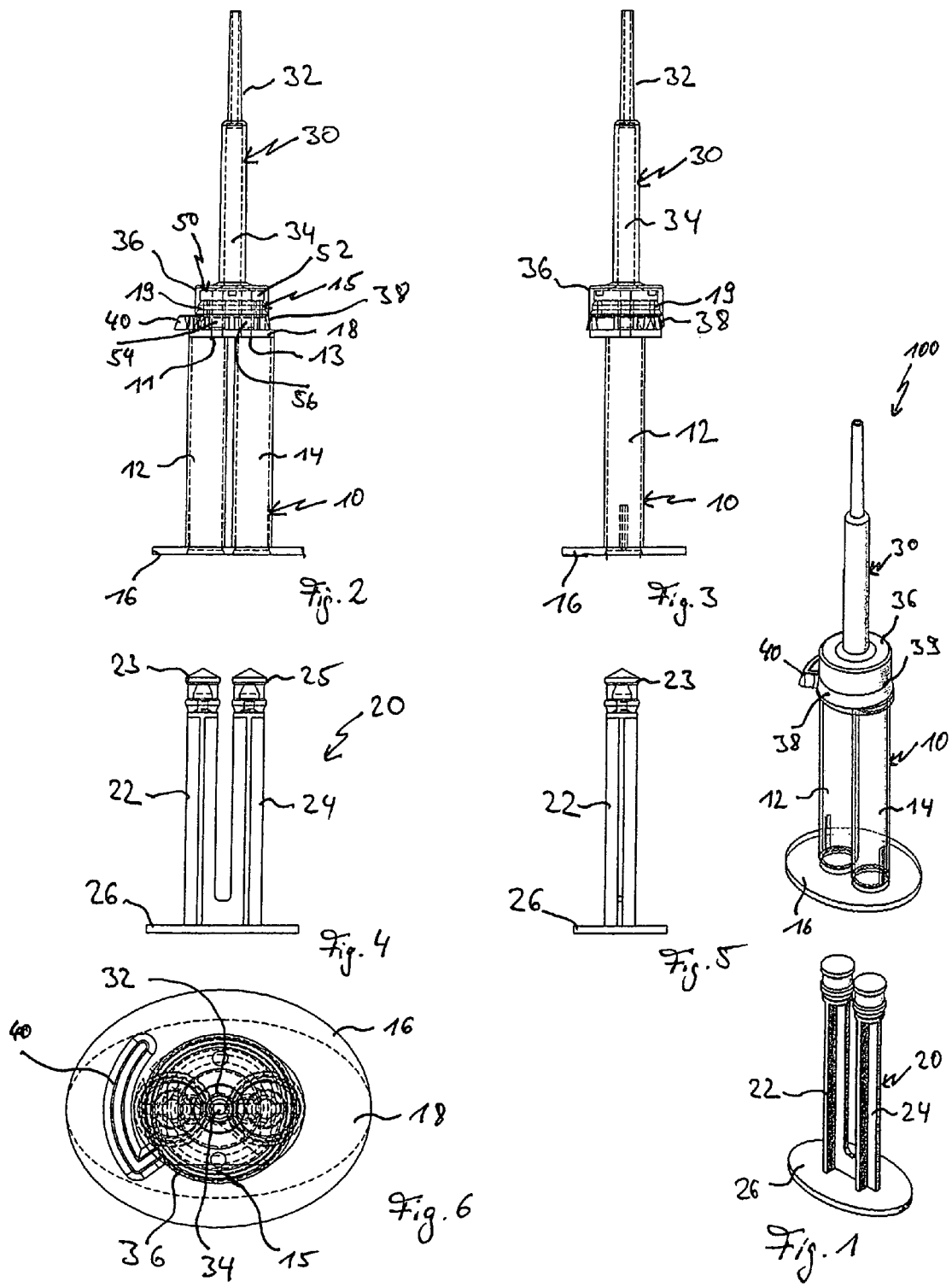

MULTICHAMBER DISPENSING DEVICE

CROSS REFERENCES TO RELATED APPLICATIONS

This application claims the priority benefit of European Patent Application No. 05 015 995.3 filed on Jul. 22, 2005.

STATEMENT REGARDING FEDERALLY SPONSORED RESEARCH

Not Applicable.

TECHNICAL FIELD

The invention relates to a multichamber dispensing device for dispensing a mixture made up of several substances, and in particular to a multichamber dispensing device including a receptacle unit with several chambers that are aligned parallel to each other, each of which has an open first end for inserting a piston and a second end which comprises an outlet opening, and a dispensing unit comprising a dispensing channel and an adapter section, which is connected leak proof to the receptacle unit.

DESCRIPTION OF THE BACKGROUND ART

A multiple chamber dispensing device having a multichamber dispensing device including a receptacle unit with several chambers that are aligned parallel to each other, each of which has an open first end for inserting a piston and a second end which comprises an outlet opening, and a dispensing unit comprising a dispensing channel and an adapter section, which is connected leak proof to the receptacle unit is known from EP 1 203 593 A1. Unfortunately, the dispensing device disclose in the EP reference is a throw-away article suitable only for one-time use.

SUMMARY OF THE INVENTION

The object of the present invention is to create a multichamber dispensing device that is suitable for repeated use, and which can be handled easily and be manufactured cost-effectively. This object is accomplished in one embodiment of the invention by providing a multichamber dispensing device for dispensing a mixture made up of several substances, as disclosed herein. In particular, the device includes a receptacle unit with several chambers that are aligned parallel relative to each other, each of which has an open first end for inserting a piston and a second end which comprises an outlet opening, and with a dispensing unit, comprising a dispensing channel and an adapter section, which is connected to the receptacle unit and into which particularly the receptacle unit engages in order to connect the dispensing unit with the receptacle unit. The adapter section of the dispensing unit comprises at least one detachable separating element which protrudes radially to the inside, which element interacts with at least one locking means of the receptacle unit. After loosening the separating element, the dispensing unit opposite the receptacle unit can be shifted in an axial direction.

Advantageously, the dispensing unit is secured to the receptacle unit by means of the separating element, so that no unintentional relative motion between the two units can occur. Relative motion for loosening the dispensing unit from the receptacle unit, for instance, can consequently occur only after loosening the separating element.

The multichamber dispensing device, which can essentially be designed in the form of a syringe, is particularly intended for repeated use, whereby the dispensing unit can be changed for each use. For this purpose, the separating element is loosened prior to changing the dispensing unit, so that the dispensing unit can essentially be separated from the latter without resistance and without damage to the receptacle unit.

When using the multichamber dispensing device, the substances contained in the individual chambers can mix downstream of the outlet openings of the chambers and upstream of the dispensing channel, or in the dispensing channel of the dispensing unit. The chambers of the receptacle unit can exhibit different or equal volumes, so that a desired mixing ratio between the separate substances that are held in the chambers can be adjusted by appropriate design of the respective outlet openings. By pushing a piston, the substances are conveyed from the chambers of the receptacle unit into the dispensing unit and its dispensing channel, from where they can then be applied in a mixed form.

A preferred embodiment of a device incorporating the present invention includes a separating element provided with a band-like separating strip which projects radially to the inside, which encloses the receptacle unit, and which at least for the most part can be separated from the dispensing unit by pulling. In order to provide a user of the multichamber dispensing device with convenient means for separating and/or replacing the dispensing unit from the receptacle unit, the separating element preferably comprises at least one pull-tab, which can be easily gripped by the user.

The locking means provided on the receptacle unit can secure the dispensing unit either in a neutral position, in which the substance stream between the chambers of the receptacle unit and the dispensing channel of the dispensing unit is blocked, and/or in a dispensing position, in which the substances contained in the chambers can, by pushing on the pistons, be conveyed via the outlet openings to the dispensing channel, from whence they can be applied. A particularly effective securing means against shifting the dispensing unit opposite the receptacle unit is ensured if the locking means of the receptacle unit is designed as an annular flange.

In order to bring the dispensing unit easily into the neutral position, it is advantageous if the locking means is provided with a bevel on the side facing away from the neutral position.

The dispensing unit can, for example, be secured to the receptacle unit in such a way that the dispensing unit can be separated from the receptacle unit by loosening the separating element. Alternatively, or also additionally, the securing means can be designed so that by loosening the separating element the dispensing unit and the receptacle unit can be made telescopic, i.e. collapsible.

In a special embodiment, the multichamber dispensing device is modified in the collar area of the receptacle unit, which is positioned downstream of the outlet openings of the chambers of the receptacle unit. The collar area particularly serves for fastening the dispensing unit, and thus, preferably exhibits an outside diameter that essentially corresponds to the inside diameter of the adapter section of the dispensing unit.

In order to ensure accurate angular positioning when mounting the dispensing unit on the receptacle unit, the collar area, for example, exhibits a groove-like or lug-like positioning means, which interacts with a corresponding lug-like and/or groove-like positioning means of the adapter section of the dispensing unit.

A connecting unit can be provided as an insert in the dispensing unit to control the fluid stream between the chambers and the dispensing channel. In order to prevent unintentional mixing of the substance in the chambers of the receptacle unit downstream of the outlet openings, the dispensing unit, in a special embodiment, preferably incorporates a closure unit for the outlet openings of the chambers, which unit is formed within the connecting unit.

The connecting unit can include a stopper for each outlet opening of each of the chambers. A closure unit can be provided including multiple stoppers. The individual stoppers can protrude from a plate-like section of the connecting unit in the direction of the respective chamber of the receptacle unit.

In order to be able to separate the connecting unit together with the dispensing unit from the receptacle unit and to change it in a simple manner, it is preferably locked by means of a plate-like section in the dispensing unit. The locking of the connecting unit in the dispensing unit is preferably torque-resistant, so that the positioning of the connecting unit relative to the receptacle unit is also predetermined by the angular positioning of the dispensing unit relative to the receptacle unit.

The stoppers can be designed in such a way that when the dispensing unit is in the dispensing position they release a substance stream from the chambers of the receptacle unit into a mixing chamber in the dispensing unit, which chamber is provided with a static mixer. The mixing chamber can be formed from the dispensing channel or can also be arranged upstream of the dispensing channel.

For this purpose, each stopper can be provided with a cross-channel, which is connected to a blind-hole axial channel in the respective stopper leading to the mixing chamber.

Furthermore, a shoulder protruding crosswise can be molded onto the plate-like body of the connecting unit. The shoulder cooperates with a longitudinal groove inside the collar area in such a way that the connecting unit together with the dispensing unit can be mounted on and/or within and/or inserted in the collar area only in a predetermined angular position in which the closing stoppers of the connecting unit align with their corresponding outlet openings of the chambers.

Further advantages and advantageous embodiments of the subject matter of the invention can be found in the specification, the drawing and the claims.

BRIEF SUMMARY OF THE DRAWINGS

Two exemplary embodiments of a multichamber dispensing device incorporating the present the invention are schematically represented in a simplified form in the following drawing and are described in further detail below:

FIG. 1 is a perspective representation of a multichamber dispensing device design taught by the invention;

FIG. 2 is a longitudinal section through a receptacle unit with a mounted dispensing unit of the multichamber dispensing unit according to FIG. 1;

FIG. 3 is a longitudinal section of the assembly consisting of the receptacle unit and the dispensing unit, rotated by 90°;

FIG. 4 is a side view of a piston unit of the multichamber dispensing unit according to FIG. 1;

FIG. 5 is a side view of the piston unit, rotated by 90°;

FIG. 6 is a plan view of the multichamber dispensing device according to FIG. 1 in axial direction;

DETAILED DESCRIPTION OF THE PREFERRED EMBODIMENTS

Figure 8:
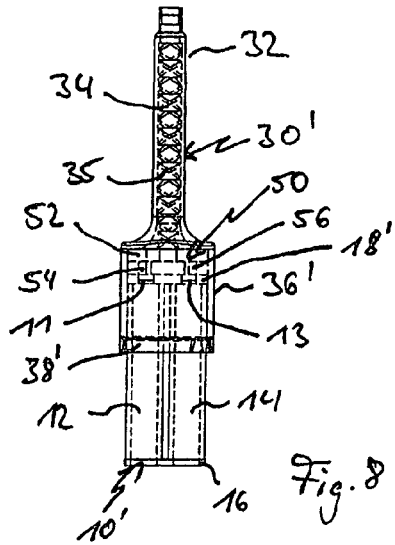
FIG. 8 is a longitudinal section through a receptacle unit with a mounted dispensing unit of the multichamber dispensing unit according to FIG. 7.
Figure 9:
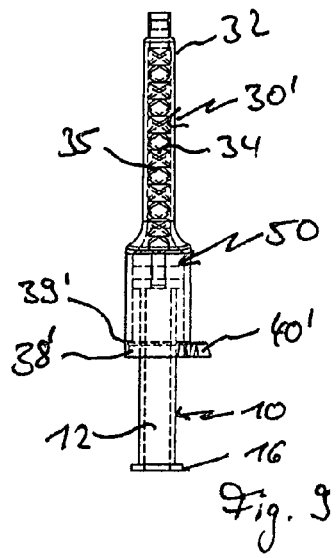
FIG. 9 is a longitudinal section of the assembly illustrated in FIG. 8, rotated by 90°.
Figure 10:
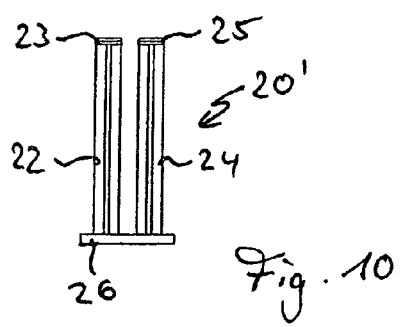
FIG. 10 is a side view of a piston unit of the multichamber dispensing unit according to FIG. 7.
Figure 11:
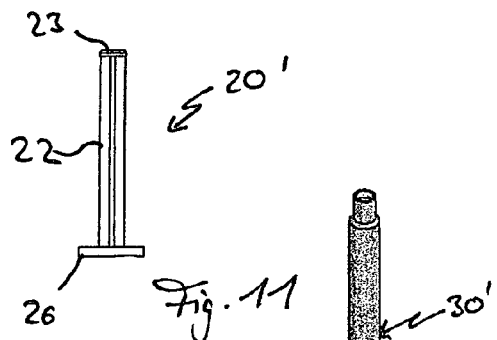
FIG. 11 is a side view of the piston unit according to FIG. 10, rotated by 90°.
Figure 12:
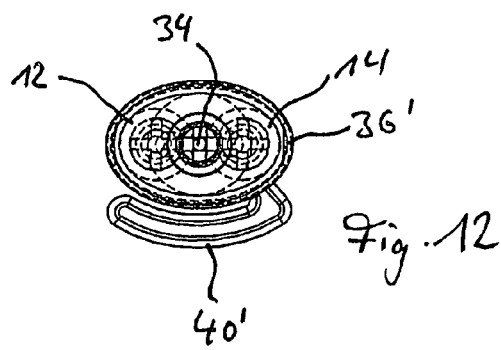
FIG. 12 is a plan view of the multichamber dispensing device according to FIG. 7 in axial direction.
Figure 7:
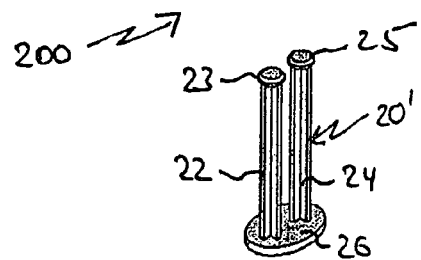
FIG. 7 is a perspective representation of a second embodiment of the multichamber dispensing device taught by the invention.

FIGS. 1 to 6 illustrate a multichamber device 100 designed as a two-chamber ampoule including a receptacle unit 10, a piston unit 20 and a dispensing unit 30. Although a two-chamber ampoule is described, the multichamber device can include more than two chambers without departing from the scope of the invention.

The vessel-shaped receptacle unit 10 comprises two tubular chambers 12 and 14 positioned in parallel adjacent to each other, which extend in an axial direction of dispensing unit 10. The chambers 12 and 14 are open across their entire cross-section in each of their first ends, which are shown at the bottom of the drawing. A back plate 16 is molded onto the exterior of the first ends of chambers 12 and 14 and extends in a transverse and/or radial direction. The second ends of the chambers 12 and 14, facing away from the first ends, are connected to each other by means of a molded front plate 18. A first outlet opening 11 for chamber 12 and a second outlet opening 13 for chamber 14 are formed in the front plate 18.

A collar area 15 framing the outlet openings 11 and 13 is substantially cylindrical and molded onto the front plate 18 on the side facing away from chambers 12 and 14. The axis of the collar area 15 is arranged in parallel to the axes of chambers 12 and 14. In the present exemplary embodiment, chambers 12 and 14 have the same cross-section. Accordingly, the outlet openings 11 and 13 also have the same cross-section. Alternatively, one of the chambers could also have a larger cross-section, in which case the outlet opening assigned to this chamber should also have a larger cross-section than the outlet opening assigned to the other chamber.

As shown in FIGS. 4 and 5, the piston unit 20 comprises two piston rods 22 and 24, whose rear ends are connected to each other by means of a pusher plate 26. A piston 23 for chamber 14 is formed on the front end of the piston rod 22. A piston 25 for chamber 14 is formed on the front end of the piston rod 24. Since the multichamber dispensing device 10 is symmetrical in form, piston rods 22 and 24 can also be assigned to chambers 12 and 14 in the reverse order. Pistons 23 and 25 inserted into the rear open ends of chambers 12 and 14 sealingly engage the chambers 12 and 14 and can be moved synchronously inside them.

The dispensing unit 30 comprises a cannula-like, stepped tube section 32, in which a dispensing channel 34 leads into the free end as shown in the top of the drawing FIG. 3, as well as an adapter section 36, which is mounted on the collar area 15 of the receptacle unit 10 and which is essentially also cylindrical in form.

In order to fasten the dispensing unit 30 on the collar area 15 of the receptacle unit 10, the adapter section 36 comprises a separating strip 38 on its end facing the receptacle unit 10 which extends along its circumference and projects radially to the inside and which is locked on an annular flange 19 of the collar area 15 of the receptacle unit 10. The separating strip 38 can be separated from the remaining adapter section 36 along a separating seam 39 which runs around its circumference. A pull-tab 40 is provided for this purpose, which can be easily gripped by a user.

The annular flange 19, which represents a locking means, is beveled on the side facing away from chambers 12 and 14, allowing the dispensing unit 30 with a separating strip 38 to be easily pushed onto the collar area 15 of receptacle unit 10. Advantageously, through the interaction of the separating strip 38 projecting radially to the inside and the annular flange 19, the separating strip 38 is locked relative to the annular flange 19.

A connecting unit 50 arranged in the adapter section 36 of the dispensing unit has a leaf-like design and includes a plate-like section 52 that extends in a radial direction. The plate-like section 52 serves to lock the connecting unit 50 into the adapter section 36.

Two plugs and/or stoppers 54 and 56 protrude from the connecting unit 50 into the direction facing away from the dispensing channel 34. Each stopper 54 and 56 has an axial channel connected through the outlet openings 11 and 13 with chambers 12 and 14. Both axial channels lead from the outlet openings 11 and 13 to the face end of plate 52, which is facing away from chambers 12 and 14, so that the two substances held in chambers 12 and 14 can mix downstream of plate 52 upon activation of the piston unit 20. A static mixer can be arranged in the dispensing channel 34 in order to assist this process. The static mixer is secured in the dispensing channel 34 through the locked-in connecting unit 50.

The collar area 15 of receptacle unit 10 furthermore includes a guide lug which cooperates with a corresponding recess on the inside of the adapter section 36 of the dispensing unit 30. The guide lug is a positioning device by means of which the dispensing unit 30 can be accurately angularly positioned (i.e. circumferentially) relative to the receptacle unit 10. The connecting unit 50 is furthermore provided with a locking lug which interacts with a corresponding recess on the inside of the adapter section 36, locking the connecting unit 50 torque-resistantly into the dispensing unit 30.

Prior to using the multichamber dispensing device 100, the outlet openings 11 and 13 of chambers 12 and 14 of the receptacle unit 10 are initially closed by a cover element. The piston unit 20 is inserted into the chambers 12 and 14. Each of chambers 12 and 14 are filled with one component of a two-component system, such as used for dental applications, for example. In order to apply the two-component system, the cover element is taken off the receptacle unit 10, and the dispensing unit 30 is mounted on the collar area 15. In this way, the connecting unit 50 through its axial channels provides a connection between the dispensing channel 34 representing a mixing chamber and the outlet openings 11 and 13 of chambers 12 and 14. The separating strip 38 is then locked on the annular flange 19 of the collar area 15.

By applying pressure to the pusher plate 26 of the piston unit 20, the individual components in chambers 12 and 14 are conveyed via the connecting unit 50 to the dispensing channel 34 and applied in a mixed form through its opening in the end face that is facing away from the adapter unit 36. In this way, chambers 12 and 14 are, for example, only partially emptied, so that chambers 12 and 14 still contain sufficient material for a further application. In this case, the user can keep the assembled multichamber dispensing device 100, so that the mixed components downstream of platelet 50 can cure. The cured material securely closes chambers 12 and 14 and/or their outlet openings 11 and 13.

For repeated use of the multichamber dispensing device 100, the user grips the pull-tab 40 and pulls off the separating strip 38 along the separating seam 39 from the remaining adapter unit 36. This unlocks the dispensing unit 30. This can now be separated from the collar area 15 of the receptacle unit 10. Thereafter, a new dispensing unit 30 is mounted on the receptacle unit 10 in the manner described above, so that any remaining components of the two-component system in chambers 12 and 14 can be discharged through the dispensing unit 30 by a renewed application of pressure on the pusher plate 26 of the piston unit 20.

FIGS. 7 to 12 show a second embodiment of the multiple chamber dispensing device incorporating the present invention. This multichamber dispensing device 200 is essentially made up from three components according to the embodiment represented in FIGS. 1 to 6, which is comprised of a receptacle unit 10', a piston unit 20' and a dispensing unit 30'. The multichamber dispensing device 200 differs from the one according to FIGS. 1 to 6 in that the dispensing unit 30' does not exhibit a collar area, but that instead a faceplate 18', in which the outlet openings 11 and 13 for the chambers 12 and 14 of the receptacle unit 10' are arranged, represents the boundary of the receptacle unit 10' facing away from the piston unit 20'.

The dispensing unit 30' includes an adapter section 36', which essentially has an oval cross-section and which accepts the end sections of the receptacle unit 10' facing away from the piston unit 20'. As in the embodiment shown in FIGS. 1 to 6, the dispensing unit 30' comprises a tubular section 32 including a dispensing channel 34, which accommodates a static mixer 35. The static mixer 35 is secured to the dispensing channel 34 by a connecting unit 50' representing a closure unit, which exhibits a plate-like section 52, by means of which it is secured in the dispensing unit 30'.

Figure 13:
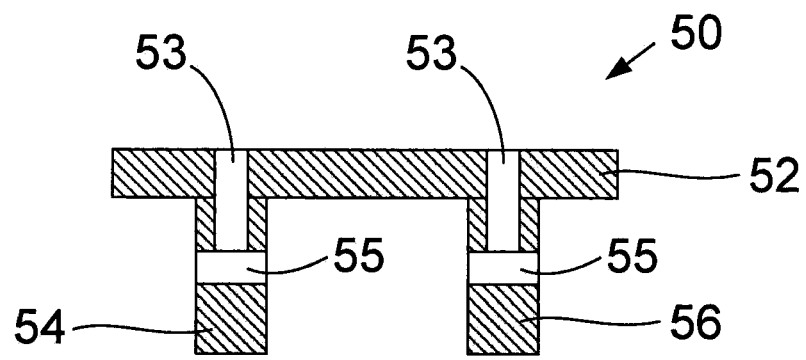
FIG. 13 is a cross sectional view of the connecting unit of FIG. 2.
Figure 14:
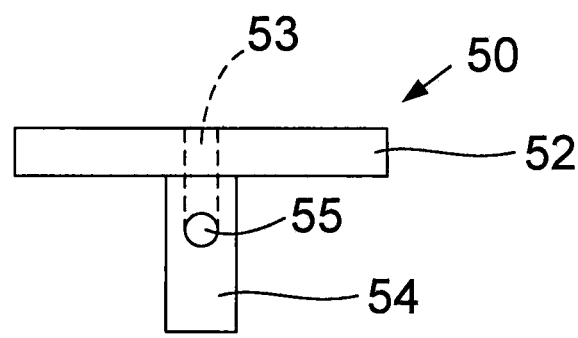
FIG. 14 is an end view of the connecting unit of FIG. 13.

Two sealing plugs 54 and 56 protrude from the plate-like section 52 in the direction of chambers 12 and 14. As shown in FIGS. 13 and 14, the plugs 54 and 56 are each provided with an axial channel 53 and a cross-channel 55 and extend into the outlet opening 11 and 13 of chambers 12 and 14. In a closing position, the sealing plugs 54 and 56 close the outlet openings 11 and 13.

In the opening position, i.e., when the sealing plugs 54 and 56 enter into chambers 12 and 14, the cross-channels 55 of sealing plugs 54 and 56, which are arranged in the respectively assigned chamber 12 and/or 14 of the receptacle unit 10', each channel 55 defines a fluid stream between the chamber 12 and/or 14 and the dispensing channel 34. By applying pressure to the pusher plate 26 of the piston unit 20' the fluid stream conveys the components of a two-component system held in the chambers 12 and 14, via the cross-channels 55 and axial channels 53 of the sealing plugs 54 and 56, through the closure unit 52, to the mixing space forming the dispensing channel 34. The components are then applied in a mixed form through this channel 34.

The adapter section 36' of the dispensing unit 30 exhibits in its end section, facing away from the tubular section 30, a separating strip 38' that represents a separating element. The separating strip 38' encloses both chambers 12 and 14 of the receptacle unit 10' and is provided with a pull-tab 40. The separating strip 38' protrudes radially to the inside and interacts with a stop lug formed on chambers 12 and 14. After loosening the separating strip 38' from the remaining adapter section 36' along a separating seam 39', the dispensing unit 30' and thus the closure unit 50' locked into it can be shifted in the direction of the end of the receptacle unit 10' facing the piston unit 20', so that there exists an activation position having a fluid connection between chambers 12 and 14 on the one hand and between the dispensing channel 34 on the other. The separating strip 38 consequently secures the dispensing unit 30 and thus the closure unit 50' in the closed position. After loosening the separating strip 38', the receptacle unit 10' and the dispensing unit 30' can be telescoped.

I claim:

1. A multichamber dispensing device for dispensing a mixture made up of several substances, comprising:
   a receptacle unit with several chambers that are aligned parallel to each other, each of which has an open first end for inserting a piston and a second end which comprises an outlet opening;
   a dispensing unit, comprising a dispensing channel and an adapter section, which is connected to the receptacle unit, wherein the adapter section includes at least one detachable, separating element that protrudes radially to the inside, which interacts with at least one locking means of the receptacle unit, and which, after loosening the separating element, allows the dispensing unit opposite the receptacle unit to be shifted in an axial direction; and
   a connecting unit disposed in the adapter section and having an open position and a closed position, said connecting unit including a plate-like section and several plugs, each of said plugs corresponding to one of said several chambers of said receptacle unit and extending from said plate-like section away from said dispensing channel toward said outlet opening of said one of said several chambers of said receptacle unit, each of said plugs including an axial channel extending into said plug and through the plate-like section and a cross-channel intersecting said axial channel, wherein in said closed position, said plug closes said one of said outlet openings, and in said open position, said plug extends through said one of said outlet openings and said cross-channel is in fluid communication with said one of said several chambers of said receptacle unit allowing a substance in said one of said several chambers to pass through said cross-channel into said axial channel and past said plate-like section to mix downstream of said plate-like section with a substance from another of said several chambers.

2. The multichamber dispensing device according to claim 1, in which the separating element is a separating strip that projects radially to the inside, that encloses the receptacle unit and that can be separated at least for the most part from the dispensing unit.

3. The multichamber dispensing device according to claim 1, in which the separating element exhibits a pull-tab.

4. The multichamber dispensing device according to claim 1, in which the locking means secures the dispensing unit in a neutral position and/or in a dispensing position.

5. The multichamber dispensing device according to claim 1, in which the dispensing unit can be separated from the receptacle unit through loosening of the separating element.

6. The multichamber dispensing device according to claim 1, in which the dispensing unit and the receptacle unit can be made to telescope through loosening of the separating element.

7. The multichamber dispensing device according to claim 1, in which the locking means is provided with a bevel on an outside face.

8. The multichamber dispensing device according to claim 1, in which the locking means of the receptacle unit is developed as an annular flange.

9. The multichamber dispensing device according to claim 1, in which the locking means is developed on a collar area of the receptacle unit, which is arranged downstream of the outlet openings of chambers of the receptacle unit.

10. The multichamber dispensing device according to claim 1, in which a positioning device located on the receptacle unit is aligned relative to the receptacle unit, by means of the dispensing unit, through cooperation with a corresponding positioning means on the adapter section (36) of the dispensing unit.

11. The multichamber dispensing device according to claim 1, in which the connecting unit is preferably locked torque-resistant in the dispensing unit.

12. The multichamber dispensing device according to claim 1, in which each of the plugs in their dispensing position release a substance stream to a mixing chamber.

13. The multichamber dispensing device according to claim 1, in which the connecting unit secures a static mixer in the dispensing unit.

14. A multichamber dispensing device for dispensing a mixture made up of several substances, comprising:
   a receptacle unit with at least two chambers aligned parallel to each other, each of said chambers having an open first end for receiving a piston and a second end having an outlet opening; and
   a dispensing unit connected to the receptacle unit and including an adapter section, said adapter section including at least one detachable, separating element that protrudes radially inwardly and engages said receptacle unit, wherein after disengaging said separating element from said receptacle unit, said dispensing unit is movable in an axial direction relative to said receptacle unit; and
   a connecting unit disposed in the adapter section and having an open position and a closed position, said connecting unit including a plate-like section and several plugs, each of said plugs corresponding to one of said several chambers of said receptacle unit and extending from said plate-like section away from said dispensing channel toward said outlet opening of said one of said several chambers of said receptacle unit, each of said plugs including a first channel extending into said plug and through the plate-like section, wherein in said closed position, substances in said several chambers are blocked from passing through said first channel, and in said open position, a substance in one of said several chambers passes into said first channel and past said plate-like section to mix downstream of said plate-like section with a substance from another of said several chambers, in which each of said plugs include a second channel intersecting said first channel, wherein in said closed position, said plug closes said one of said outlet openings, and in said open position, said plug extends through said one of said outlet openings and said second channel is in fluid communication with said one of said several chambers of said receptacle unit allowing a substance in said one of said several chambers to pass through said second channel into said first channel and past said plate-like section to mix downstream of said plate-like section with a substance from another of said several chambers.

* * * * *